United States Patent [19]

Cisar

[11] Patent Number: 5,151,515

[45] Date of Patent: Sep. 29, 1992

[54] OXYGEN REDUCTION CATALYST BASED UPON METAL DIPYRIDYLAMINES

[75] Inventor: Alan J. Cisar, Sugar Land, Tex.

[73] Assignee: The Dow Chemical Company, Midland, Mich.

[21] Appl. No.: 650,355

[22] Filed: Feb. 4, 1991

[51] Int. Cl.$^5$ .......................... C07F 15/06; B01J 31/18; H01M 4/88

[52] U.S. Cl. ........................ 546/12; 502/167; 502/101; 502/180; 502/200; 429/12; 429/42; 429/43

[58] Field of Search ............................. 546/12

[56] References Cited

U.S. PATENT DOCUMENTS

| | | | |
|---|---|---|---|
| 3,585,079 | 6/1971 | Richter et al. | 136/86 A |
| 3,996,164 | 12/1976 | Matsuda | 546/2 |
| 4,153,795 | 5/1979 | Matsuda | 546/2 |
| 4,255,498 | 3/1981 | Yoshida | 429/27 |

OTHER PUBLICATIONS

Johnson, Inog. Chem. Acta 18, 664(1979).
Rob van Veen et al., Journal Chemical Society; Faraday Trans. 1, 1981, 77, pp. 2827-2843.

*Primary Examiner*—Mark L. Berch

[57] ABSTRACT

A supported metal catalyst useful in the preparation of an electrode for an electrochemical cell comprises the residue after pyrolysis of an organometallic complex which is the reaction product of a transition metal salt or noble metal salt and at least one of 2,2′ dipyridylamine or substituted derivative thereof.

2 Claims, 1 Drawing Sheet

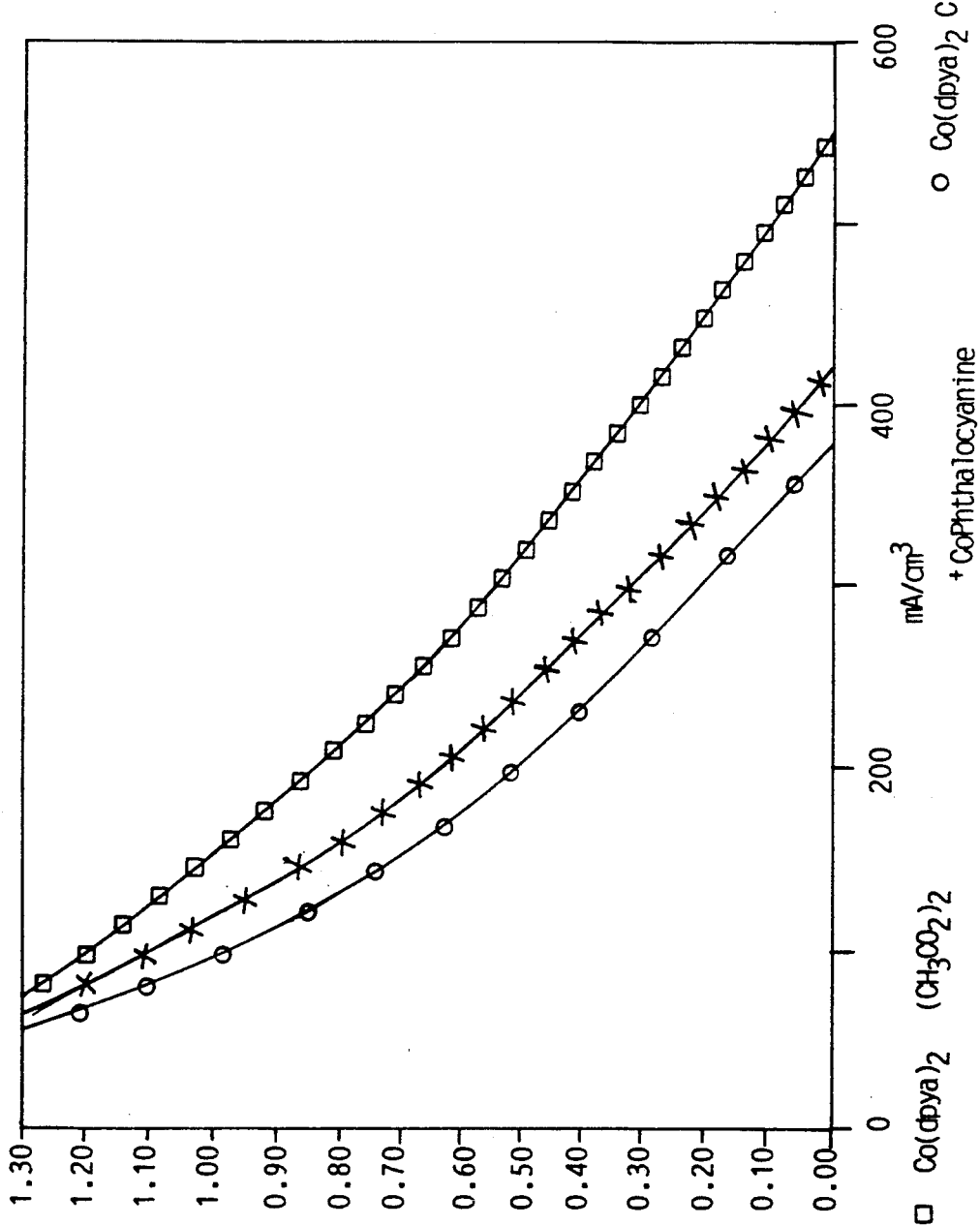

OXYGEN REDUCTION CATALYST BASED UPON METAL DIPYRIDYLAMINES

BACKGROUND OF THE INVENTION

1. Field of the Invention

This invention relates to catalytic electrodes for electrochemical cells.

2. Description of the Prior Art

The term "fuel cell" is used herein and in the art to denote a device, system, or apparatus in which the chemical energy of a fluid combustible fuel such as hydrogen, carbon monoxide, or an organic compound containing hydrogen in its molecular structure is electrochemically converted to electrical energy at a nonsacrificial or inert electrode. The true fuel cell is adapted for continous operation and is supplied with both fuel and oxygen from sources outside the cell proper. Such cells include at least two nonsacrificial or inert electrodes, functioning as an anode and a cathode, respectively, which are separated by an electrolyte which provides ionic conductance therebetween. There is also provided conduction means for electrical connection between anode and cathode external to the electrolyte, means for admitting a fluid fuel into dual contact with the anode and electrolyte, and means for admitting oxygen in dual contact with the cathode and electrolyte. Where necessary or desired, the electrolyte compartments are divided into an anolyte and catholyte compartment by an ion permeable partition or ion exchange membrane or plurality of same. In each such cell, a fuel is oxidized at the anode and an oxidant is reduced at the cathode upon receiving electrons from the anode.

Electrodes of the type hereinbefore and hereinafter described are also employed in electrolytic cells which unlike the aforementioned fuel cells do not provide a net production of electrical energy, but in which an organic fuel is oxidized electrochemically at the anode thereof. In such cells, a direct current of electrical energy from an external source, namely a fuel cell, a storage battery or an alternating current rectifier, is admitted to the electrical circuit of the cell to provide the necessary electrical current to operate the cell. Such cells can be used for the electrochemical production of various organic chemicals, such as the conversion of alcohols or hydrocarbons to ketones.

Electrodes for use in these cells vary considerably in both design and composition. Although a single metal structure, such as a platinum sheet or screen, or a structure of porous carbon, such as a flat sheet or a porous carbon cylinder, can be used alone, electrodes commonly comprise a conductive base or current collector with a metal catalyst chemically and/or physically bound to the surface of the base. Such electrodes also include those upon which the catalyst is laid down by electro- deposition, and those which are impregnated with catalyst by soaking the base in a solution comprising a suitable catalyst yielding material, decomposing the adsorbed material and/or reducing the resulting metal-containing material to elemental metal or metal oxide. The latter technique is conventional in the preparation of porous carbon electrodes bearing a metal catalyst. Noble metals, particularly platinum, are effective catalysts in both oxidation-reduction reactions wherein either a basic or acid electrolyte is employed in the cell.

The use of monomeric, as well as, polymeric metal phthalocyanine compounds as oxidation catalysts for chemical reactions are known. For example, nickel phthalocyanine has been employed in the oxidation of long-chain fatty acids, esters, saturated ketones, benzene hydrocarbons, etc. Such catalysts, particularly cobalt phthalocyanine, when used as an active component in the cathode of a fuel cell are advantageous over known electrode catalysts comprised of noble metals, primarily in that the cobalt phthalocyanine catalyst is relatively inexpensive and can be produced in any desired amount. One disadvantage of electrodes comprising cobalt phthalocyanine is that this compound has an extremely low conductivity in comparison with noble metal catalyst compositions and, therefore, such metal phthalocyanine catalyst must be applied in very thin layers upon the surfaces of conducting carrier material in the preparation of electrodes. Electrochemical cells having electrodes comprising cobalt phthalocyanine, are disclosed in U.S. Pat. No. 3,585,079 and U.S. Pat. No. 4,255,498. Cobalt phthalocyanine catalysts are also disclosed in *J. Chem. Society; Faraday trans.* 1, 77, 2827–2843 (1981).

It is conventional to prepare electrodes for electrolytic cells by mixing powdered or granular active carbon particles which act as a carrier or support material for the adsorbed catalyst layer. Such electrodes are prepared by mixing the catalyzed carbon particles with a water-repellent binder such as polytetrafluorethylene and compressing the mixture into a thin sheet. Alternatively, it is conventional to utilize catalyst compositions in admixture with conductive, pulverulent material, wherein said pulverulent material is held between two porous, electricity conducting plates, such as, metal plates or nets and the assembly held together utilizing a frame comprised of insulating material; the whole assembly being pressed together to result in a fuel battery.

SUMMARY OF THE INVENTION

There are disclosed, novel organometallic complexes derived from the reaction product of a transition metal salt or noble metal salt and 2,2' dipyridylamine or substituted derivative thereof. These complexes are useful as oxygen reduction catalysts and in the preparation of electrodes for electrochemical cells, preferably, fuel cells for converting hydrogen and oxygen to energy. The novel catalyst complexes can be adsorbed on a support or contact material, such as metal, graphite, or carbon powders, and mixed with a water-repellant binder, such as, a fluorinated hydrocarbon polymer, for instance, polytetrafluoroethylene and, thereafter, coated directly or indirectly onto a current collector such as a carbon fiber paper in order to make an assembly suitable for use as an electrode for an electrochemical cell. The novel organometallic complexes can also be coated onto a nonporous substrate and the coating transferred to a porous, conductive material serving as a current collector, such as, carbon fiber paper or a nickel screen or transferred to a solid polymer electrolyte ion exchange membrane.

Prior to use of the novel organometallic complexes adsorbed on a support material as catalysts, the complexes are heated under an inert atmosphere or under vacuum to a temperature of 350°–950° centigrade.

DESCRIPTION OF THE DRAWING

The FIGURE shows current-voltage curves for representative electrodes of the invention in comparison with an electrode prepared using the cobalt phthalocyanine catalyst of the prior art.

DETAILED DESCRIPTION OF THE INVENTION

Solid polymer electrolyte electrodes can be prepared either as individual components or in association with an ion exchange membrane or current collector by bonding, to at least one side of an ion exchange membrane or current collector, a catalyst coating comprising the residue after heating of the organometallic complex of the invention and supporting material with a water-repellent binder, such as, polytetrafluoroethylene. The current collector having a catalyst coating can be a carbon fiber paper, a metal or a graphite layer. The coated side of the current collector can also be bonded to an ion exchange membrane utilizing a combination of heat and pressure. Such an electrode forms one embodiment of the electrode of the invention which is useful in a solid polymer electrolyte electrolytic cell.

The supported transition metal or noble metal 2,2' dipyridylamine, or substituted derivative thereof, catalyst of the invention, provides results which are superior when utilized in an electrochemical cell in comparison with the cobalt phthalocyanine catalysts of the prior art.

Another embodiment of the catalyst of the invention is prepared by adsorbing onto a finely divided metal, carbon, or graphite, preferably, powdered or granulated active carbon, a solution comprising an organic solvent containing a transition metal or noble metal salt in admixture with 2,2' dipyridylamine or substituted derivative thereof. Substituted derivatives of 2,2' dipyridylamine, which are considered to provide equivalent results, are the 1-5 carbon atom alkyl substituted or 5-10 carbon atom aryl substituted derivatives or mixtures of such derivatives. It is within this invention to utilize mixtures of transition metals and noble metal salts, as well as mixtures of the organic ligand and substituted derivatives.

Useful transition metals include iron, cobalt, nickel, molybdenum, chromium, manganese, tungsten, titanium, zinc, copper, cadmium, and vanadium. Useful noble metals include platinum, iridium, rhodium, palladium, ruthenium, and osmium.

Various cobalt salts have been found to be particularly useful in the preparation of the catalyst of the invention. These include cobalt chloride, cobalt acetate, cobalt nitrate, cobalt perchlorate, cobalt chlorate, cobalt bromide hexahydrate, and cobalt sulphate heptahydrate. Other cobalt compounds which are soluble in polar or donor type organic solvents can be used. Similar salts of the remaining transition metals listed above and the noble metals listed above are useful.

Generally, the formulation of the organometallic complex can take place at ambient temperature and pressure in a solution comprising an organic solvent, such as, methanol, ethanol, N-methyl pyrrolidine and dimethylsulfoxide (DMSO). The organic solvent used need not be anhydrous. The ratio of metal salt to 2,2' dipyridylamine, or substituted derivative thereof, is generally, in a proportion of 2:1 of the ligand to the metal salt to 3:1 of ligand to metal salt, preferably, the proportion is 2.1:1 to 2.5:1 of ligand to metal salt. If less ligand is used, the reaction cannot go to completion, and unchelated or partially chelated metal ions will remain. The use of a large excess of ligand can lead to the deposition of the inactive, nonconductive ligand directly on the conductive support. The concentration of the reactants in the organic solvent solution is generally in the range of 0.001 to 0.2 molal, preferably, 0.03 to 0.1 molal. The removal of the solvent subsequent to the formation of the organometallic complex can be carried out by any convenient method. Preferred, is the removal of the solvent by vacuum evaporation.

Subsequent to deposition of the organometallic complex of the invention on the support or carrier material, this assembly is heated to pyrolytically bond the catalyst to the support member. Generally, heating is conducted at a temperature of about 350° to about 950° C. Preferred, is a temperature of about 450° to about 800° centigrade. During pyrolytic bonding of the organometallic complex catalyst on the support material, heating is conducted under an inert atmosphere or in a vacuum. Any inert atmosphere can be used, such as, a nitrogen atmosphere. It is noted that an oxidizing atmosphere during pyrolytic bonding will destroy the organometallic catalyst complex and eventually destroy the support material, if of carbon or graphite, during the pyrolysis step. A reducing atmosphere can reduce the transition metal to the metallic state and render the catalyst inert.

It has been found that the organometallic catalyst complex has a stoichiometric yield with respect to the metal salt compound utilized but only 60–90% of the theoretical yield with respect to the organic ligand used. Therefore, the use of excess ligand insures complete complex formation.

In the preparation of one embodiment of the supported catalyst of the invention on a carbon support, subsequent to soaking the carbon powder in a solution of the metal salt and, for instance, 2,2' dipyridylamine,- the solution comprising an organic solvent is evaporated and the coated carbon support assembly is heated to decompose the complex under a nitrogen atmosphere at a temperature of about 450° to about 800° C. for a period of 3–5 hours. The supported carbon catalyst is, thereafter, mixed with a water-repellent binder, such as polytetrafluoroethylene, and coated upon a current collector substrate, such as, a carbon fiber paper. Coating can be accomplished utilizing a metering bar or rod or coating knife in order to apply a dispersion, preferably, aqueous to one side of the carbon fiber paper.

When an electrode is prepared utilizing an ion exchange membrane, the membrane can be, preferably, selected from a class of cation exchange resins termed sulfonic acid cation exchange resins. In these membranes, the cation ion exchange groups are hydrated sulfonic acid radicals which are attached to the polymer backbone by sulfonation.

The preferred ion exchange membranes are disclosed in U.S. Pat. No. 4,478,695 and U.S. Pat. No. 4,470,889, incorporated herein by reference. These materials, on an equivalent weight basis, generally hydrate less when immersed in water at the boil, in accordance with prior art hydration procedures, than the sulfonated perfluorocarbon membranes sold under the trade designation NAFION. At equivalent weights which are better for ion transport, i.e., lower equivalent weights provide lower electrical resistance in the cell, the membranes described in the '695 and '889 patents can be hydrated to absorb about 40–50% by weight based upon the dry weight of the membrane. These more suitable membranes would have equivalent weights of about 700 to about 900.

A typical solid polymer electrode assembly can be made by first hydrating the ion exchange membrane and subsequently bonding a catalyst layer thereto utilizing heat and pressure. Generally, the hydration of the membrane is accomplished by first converting the membrane from the salt form to the proton form. The salt form (usually the sodium or potassium salt) is thus converted by placing it in a strong acid solution, such as sulfuric acid. Subsequently, the membrane is washed and boiled to insure saturation with water. The membrane/electrode assemblies are subsequently prepared by combining the hydrated proton form of the membrane with an electrode layer. The electrode layer is prepared in accordance with one embodiment of this invention by bonding to carbon fiber paper a metal dipyridylamine catalyst on a supporting carbon particle incorporating a water-repellent fluorinated hydrocarbon binder, such as, polytetrafluoroethylene. As the last step in the preparation of a solid polymer electrode assembly, a hydrated ion exchange membrane is bonded by pressing at elevated temperature to a catalyst coated current collector. Bonding is generally accomplished at a temperature of about 160-190 degrees centigrade. Alternatively, the metal dipyridylamine catalyst materials of the invention can be deposited directly upon the surface of an ion exchange membrane in the form of finely-divided particles or powders, such as a metal dipyridylamine catalyst supported on finely-divided granular or powdered carbon. Although the particle size of the supported catalytic material is not critical, a preferred range of particle size is from about 25-1000 angstrom units.

Since the catalytic particles coated upon the surface of the solid polymer electrolyte membrane must be energized for the passage of current for the electro oxidation or electro reduction of chemicals and elements, for the passage of current through the solid polymer electrolyte membrane, and the like, the catalyst particles or powder must be of the type generally classified as conductive, that is, such catalyst particles or powder must be electrically conductive.

As used herein, finely-divided means any powder form, particulate form, granular form, bead form, or any other form of catalyst or support material which may be deposited upon a carbon fiber paper, a non-porous support, or a solid polymer electrolyte membrane. The amount of catalyst material which is deposited directly or indirectly upon the surface of the carbon fiber paper or on the solid polymer electrolyte membranes in accordance with the process of the present invention, is not critical.

The catalytic particles must be fixed upon the surface of the carbon fiber paper or alternative current collector or solid polymer electrolyte membrane. Any well known fixing technique of adhering, bonding or otherwise uniting a particulate or powdered material to a surface may be used. In the prior art, bonding of electrode layers is disclosed at temperatures up to 177 degrees centigrade. Catalytic particles or powder may be fixed upon the surfaces of the carbon fiber paper or solid polymer electrolyte membrane by any one or a combination of pressure, heat, adhesive, binder, solvent, electrostatic means, and the like. The preferred process for fixing the particles of catalyst upon said surfaces is by a combination of pressure and heat.

The following examples illustrate the various aspects of the invention but are not intended to limit its scope. Where not otherwise specified throughout this specification and claims, temperatures are given in degrees centigrade and parts, percentages, and proportions are by weight.

EXAMPLE 1

In this Example there is described the synthesis of Bis-di-2,2'-pyridylamine Cobalt (II) Chloride, abreviated as $Co(dpya)_2Cl_2$ from 2,2'-dipyridylamine, abreviated as dpya and cobalt chloride.

Combine: 0.0989 g. $CoCl_2.6H_2O$
and
0.1793 g. dpya
in
8 g. Ethanol (EtOH).

The amount of dpya used in this example was a 26% excess over the stoichiometry required for the complex. The excess was included to insure that the reaction proceeded to completion rapidly, but is not required.

When the two materials were dissolved in separate containers and the solutions mixed, the following was observed: The $CoCl_2$ solution was purple to blue in color. The dpya solution was clear, with a hint of yellow. When the two solutions were combined, the new solution was orange. Some traces of a transient blue precipitate were observed during mixing, this was the insoluble $Co(dpya)Cl_2$. The orange solution was an ethanolic solution of $Co(dpya)_2Cl_2$.

If the two materials are dissolved simultaneously the same final solution results, but the colors of the intermediates are not clearly observed.

EXAMPLE 2

In this Example there is described the production of a supported oxygen reduction catalyst from $Co(dpya)_2Cl_2$.

A solution of $Co(dpya)_2Cl_2$ was prepared as described in Example 1.

This solution in the amount of 6.3 grams, containing 0.31 g. of $Co(dpya)_2Cl_2$ was diluted in 25 g. EtOH and added to 6.0 g. of high surface area carbon black (Cabot Vulcan XC-72R) which may have optionally been modified by oxidizing the surface with $CO_2$, as described by Manoharan et al., J. Appl. Electrochem. 16, 1986, pp. 403 ff., incorporated herein by reference.

The slurry was stirred, and the solvent evaporated. This evaporation was carried out in a vacuum using a rotary evaporator operating at or below room temperature.

The dried product was loaded into a ceramic boat which was inserted into a closed vessel which was connected to a manifold equipped for vacuum and gas manipulation and evacuated. This vessel was then filled with argon to a pressure such that gas expansion on heating did not raise the pressure to above 0.9 atm. The temperature was rapidly raised to 550° C., held for 1 hour, then cooled. This step served to pyrolytically bond the catalyst to the surface of the carbon support.

After cooling, the supported catalyst was suitable for fabrication into an electrode for use in a hydrogen-oxygen fuel cell. The current-voltage curve for an electrode utilizing this catalyst appears as shown in The FIGURE.

EXAMPLE 3

In this Example there is described the synthesis of Bis-di-2,2'-pyridylamine Cobalt (II) Acetate, abreviated as $Co(dpya)_2(CH_3CO_2)_2$ from cobalt acetate and 2,2'-dipyridylamine, abreviated as dpya.

Dissolve 1.10 g. $Co(CH_3CO_2)_2 \cdot 4H_2O$
in
30.0 g. EtOH.

This amount of cobalt acetate exceeded its solubility limit in ethanol (EtOH), so the reddish purple solution produced was saturated with cobalt acetate with traces remaining undissolved at the bottom. This caused no difficulty in the synthesis.

Dissolve 2.28 g. dpya
in
10.0 g. EtOH

This also exceeded the solubility limit in ethanol (which was about 8 wt %), and also caused no difficulty.

The dpya solution was added to the cobalt acetate solution, and the last traces of undissolved dpya rinsed with an additional 15.0 g. EtOH.

The orange solution produced contains a 51% excess of dpya. Spectroscopic inventigations have shown that competition from the chelating power of the acetate required about this much of an excess to insure that most of the cobalt will be coordinated to 2 molecules of dpya.

The current-voltage curve for an electrode prepared using this catalyst appears as shown in The FIGURE.

EXAMPLE 4

In this Example there is described the production of a supported oxygen reduction catalyst from $Co(dpya)_2(CH_3CO_2)_2$.

The solution from Example 3 was added to 10.0 g. of a high surface area carbon black, sold under the trade name Vulcan XC-72R by the Cabot Company.

Additional EtOH in the amount of 80 grams was added to insure that the carbon support was completely wetted with the solution and all of the material was rinsed into the bottom of the evaporation flask.

The slurry was mixed, and allowed to stand overnight and, thereafter, the solvent was evaporated in a vacuum using a rotary evaporator operated at room temperature or below until the product was reduced from a slurry to a solid, then gradually heated to about 60° C. to remove additional solvent.

EXAMPLE 5

Control, Forming No Part of This Invention

Example 4 was repeated substituting a solution of cobalt phthalocyanine in the amount of 0.44 grams dissolved in 100 grams of 96% sulfuric acid. To prepare a supported catalyst of the prior art, 5 grams of a finely divided carbon sold under the trade name Vulcan XC-72R are dispersed in 67 grams of 96% sulfuric acid. The solution of cobalt phthalocyanine and the suspension of finely divided carbon are combined and diluted with stirring with sufficient cold water to dilute the entire mixture to a volume of 500 milliliters. Approximately 410 milliliters of water are added to yield a final acid concentration of about 28%. The combined solutions are then filtered using a fritted glass filter and the filtered solids are washed with deionized water to remove access sulfuric acid. The solids obtained are reslurried in deionized water and the filtration is repeated to complete the washing. The supported catalyst solids are then dried in a vacuum desiccator.

EXAMPLE 6

This Example describes the pyrolytic bonding of a catalyst made with $Co(dpya)_2(CH_3CO)_2$ to a carbon support.

A supported $Co(dpya)_2(CH_3CO_2)_2$ catalyst was prepared as described in Example 4.

The catalyst of Example 4 in the amount of 3.7 g was loaded into a ceramic boat which was inserted into a Vycor tube which was evacuated.

The material was heated to 750° in a dynamic vacuum, held for 2 hours, and allowed to cool.

The resulting catalyst was suitable for fabrication into an electrode for use in a hydrogen-oxygen fuel cell. Such an electrode was fabricated in accordance with the process of Example 9 and its polarization curve recorded in comparison with the prior art catalyst of Example 7, shown in FIG. 1.

EXAMPLE 7

Control, Forming No Part of This Invention

The procedure of Example 6 was repeated substituting the supported catalyst of Example 5.

EXAMPLE 8

In this Example there is described the production of an oxygen reduction catalyst using $Co(dpya)_2(NO_3)_2$.

The synthesis of $Co(dpya)_2(NO_3)_2$ was similar, but not identical, to that reported by Johnson and Geldard, Inorg. Chem. 18(3) pp. 664-669, incorporated herein by reference.

Dissolve 0.84 g. $Co(NO_3)_2 \cdot 6H_2O$ in 5 g. EtOH to produce a clear reddish purple solution.

Dissolve 1.48 g. dpya (50% excess based on 2:1 stoichiometry) in 20 g. EtOH.

The solutions were combined and diluted to a total mass of 40 g. An orange precipitate formed, indicating that this solution exceeded the solubility limit in ethanol. The remaining ethanol was allowed to evaporate leaving a mass of small orange crystals on the bottom, with most of the excess ligand on the walls of the jar.

Depositing and bonding $Co(dpya)_2(NO_3)_2$ to a carbon support was accomplished as follows. $Co(dpya)_2(NO_3)_2$ in the amount of 0.1583 g was dissolved in 32 g. dimethylsulfoxide (DMSO).

This produced an orange solution. Although part of the excess ligand was removed during the crystallization and solvent evaporation, some excess was carried over into the DMSO solution.

The solution was added to 3.00 g. of high surface area carbon black, as described in Example 1.

Because of the fluffiness of the carbon black, the solution did not have a sufficient volume to completely wet it. An additional 50 g. of DMSO was added to insure that the solution completely wetted the support.

The solvent was removed by evaporation in a vacuum at a temperature of 50°-70° C. using a rotary evaporator.

Permanent bonding to the support was achieved by pyrolyzing at 550° C. in a static argon atmosphere for 1 hour, as described in Example 2.

The product is suitable for fabrication into an oxygen reduction electrode in accordance with the process of Example 9. The current-voltage curve for an electrode utilizing this catalyst appears in FIG. 1.

EXAMPLE 9

Using the carbon supported catalysts of Examples 7-9, an aqueous coating dispersion containing polytetrafluoroethylene as a binder is prepared and thereafter, coated onto a carbon fiber paper in accordance with the following procedure.

The electrode fabrication consists of two steps, first, the carbon fiber paper is wet-proofed by coating with an aqueous dispersion of polytetrafluoroethylene and thereafter, the carbon supported powder and is formed on the surface of the wet-proofed carbon fiber paper.

In wet-proofing the carbon fiber paper, a polytetrafluoroethylene loading of approximately 10-15 mg per square centimeter is used. In preparing the carbon powder supported catalyst, the polytetrafluoroethylene suspension of approximately 15% by weight on a solids basis is used as a binder and wet proofing agent. The polytetrafluoroethylene dispersion is supplied as a 60% solids dispersion by Dupont and sold under the trade name T-30. As is apparent, the polytetrafluoroethylene in the electrode catalyst layer serves the purpose of preventing the catalyst particles from being wet by the electrolyte when the electrode is used in an electrochemical cell and as an aid in rejecting the product water formed in the fuel cell. Such wetting would degrade the performance of the electrode by preventing the oxygen gas from reacting readily with the catalyst. If the catalyst particles are wet the oxygen gas would be required to diffuse through the layer of water, thus, slowing the reaction considerably.

The carbon fiber paper used in the preparation of the electrode is sold under the trade name PC-206 by The Stackpole Carbon Company. This is a high porosity carbon fiber paper having a porosity rating of approximately 80%. The paper used is typically 14 mils in thickness.

The carbon fiber paper after coating with an aqueous dispersion of polytetrafluoroethylene is dried by gentle heating, such as under a heat lamp or radiant heater, so as to apply mild heat and then the coated carbon fiber paper is heated in an oven at approximately 110 degrees centigrade for final drying. The coated paper is then heated in an oven at a temperature of approximately 325 degrees centigrade for about 30 minutes under an inert atmosphere to sinter the polytetrafluoroethylene and, thereafter, allowed to cool. The carbon fiber paper which is now wet-proofed is ready for use as a support for the catalyst layer.

Utilizing a dispersion, containing 5-20% polytetrafluoroethylene on a solids basis, deionized water and alcohol, a mixture of the carbon powder supported organometallic catalyst complex having a catalyst concentration of about 0.3% to about 1.0% by weight is prepared. The mixture is thoroughly and quickly mixed until some thickening occurs and then the dispersion mixture is applied to the wet-proofed carbon fiber paper and spread across the width of the paper using a Mayer rod, making slow passes back and forth so as to spread the mixture evenly across the paper. The electrode catalyst layer coating is dried initially using a radiant heat source and then subsequently dried in an oven held at a temperature of 100° under an atmosphere of nitrogen. After about 10 minutes at 100° centigrade, the temperature of the oven is raised to 325° centigrade so as to sinter the polytetrafluoroethylene binder over a period of 5-10 minutes of heating. Thereafter, the coated carbon fiber paper is cooled to 40° centigrade. The electrode is now ready for bonding to an ion exchange membrane.

EXAMPLE 10

This example describes an alternative procedure for preparing a catalytic layer on a non-porous substrate and the subsequent transfer of this layer to a carbon fiber paper.

A suspension of supported catalyst is prepared as described in Example 9 except that stirring is continued until the solids present coagulate. If coagulation is slow or difficult to obtain merely by stirring, coagulation can be accelerated by the addition of a water miscible organic solvent in addition to that amount of solvent which is already present. This solvent can be one of the lower alcohols represented by ethanol, isopropanol, and methanol, or various esters, ethers, and ketones. Thereafter, the water layer is decanted and the coagulum is rinsed two to three times with deionized water. The coagulum is then spread upon a clean sheet of niobium foil and allowed to dry upon exposure to a radiant heat source for about one hour. Thereafter, a sheet of wet-proofed carbon fiber paper, prepared in accordance with the procedure of Example 7, is placed upon the catalyst coating and the assembly is placed in a press at a temperature of about 40 degrees centigrade and the pressure raised to 1000 lbs. per square inch for 2-7 minutes and then released. The catalyst coating on the carbon fiber paper is removed from the press and placed in an oven at a temperature of 350° C. for 5 minutes and then removed and placed in deionized water. At this point the niobium foil can be easily removed from the assembly. The assembly is then bonded to an ion exchange membrane utilizing a press set at a pressure of 500 lbs. per square inch and a starting temperature of 40° C. The press temperature is slowly raised to 350° Fahrenheit and held for 5 minutes and the assembly is cooled while maintaining the pressure.

EXAMPLE 11

This example describes a procedure for bonding the coated wet-proofed carbon fiber paper to an ion exchange membrane in order to make a solid polymer electrolyte electrode.

An ion exchange membrane characterized as having an equivalent weight of about 800 produced by the process of U.S. Pat. No. 4,478,695 is bonded to the uncoated side of the catalyst coated wet-proofed carbon fiber paper prepared in Example 7. The membrane and carbon fiber paper having a catalyst layer are bonded by first placing a first carbon fiber paper electrode having the coated side toward the ion exchange membrane. Thereafter, the coated side of a second carbon fiber paper electrode can be placed against the opposite side of the ion exchange membrane if desired. The assembly is then placed in a press at ambient temperature. The previously formed laminate is covered on both exposed sides with release paper and the assembly is heated in a press and slowly raised to a temperature of 175° C. The assembly is pressed at a pressure of about 500 pounds per square inch. When the temperature of the press reaches the desired 175° C., the assembly is held in the press for an additional 5 minutes and then cooled while retaining the pressure. Once the unit has been cooled to approximately 50° C., the assembly is removed from the press and placed in an enclosed structure containing a small amount of deionized water until ready for use.

EXAMPLE 12

The solid polymer electrolyte electrode prepared in Example 11 is utilized in a fuel cell and is found to provide comparable results with respect to voltage for various current densities in comparison with control Example 13 which follows.

EXAMPLE 13

(Control, Forming No Part of This Invention)

Utilizing cobalt phthalocyanine as a catalyst, the procedure of Examples 7-9 is followed in order to prepare an electrode for use in a fuel cell.

While this invention has been described with reference to certain specific embodiments, it will be recognized by those skilled in the art that many variations are possible without departing from the scope and spirit of the invention. It will be understood that it is intended to cover all changes and modifications of the invention disclosed herein for the purposes of illustration, which do not constitute departures from the spirit and scope of the invention.

I claim an exclusive property or privilege in the invention defined as follows:

1. The compound Bis-di-2,2'-pyridylamine cobalt (II) chloride.

2. The compound Bis-di-2,2'-pyridylamine cobalt (II) acetate.

* * * * *